United States Patent [19]

Förster et al.

[11] Patent Number: 4,769,484

[45] Date of Patent: Sep. 6, 1988

[54] PHENOXYBENZOIC ACID ESTER HERBICIDES

[75] Inventors: Heinz Förster, Wuppertal; Theodor Pfister, Monheim; Hans-Joachim Santel, Leverkusen; Robert R. Schmidt, Bergisch-Gladbach; Robert H. Strang, Duesseldorf, all of Fed. Rep. of Germany

[73] Assignee: Bayer Aktiengesellschaft, Leverkusen, Fed. Rep. of Germany

[21] Appl. No.: 81,430

[22] Filed: Aug. 4, 1987

[30] Foreign Application Priority Data

Aug. 21, 1986 [DE] Fed. Rep. of Germany ....... 3628317

[51] Int. Cl.$^4$ .......................................... C07C 79/46
[52] U.S. Cl. ...................... 560/21; 558/415; 71/108; 71/111; 560/12; 560/16
[58] Field of Search .................. 560/21, 12, 16; 558/415; 71/108, 111

[56] References Cited

U.S. PATENT DOCUMENTS 4,063,929 12/1977 Bayer et al. ........................... 560/21
4,448,982 5/1984 Liu et al. ............................. 560/21

FOREIGN PATENT DOCUMENTS 34883 9/1981 European Pat. Off. .
66106 12/1982 European Pat. Off. .
0092112 10/1983 European Pat. Off. .
3531006 3/1987 Fed. Rep. of Germany .
2068948 8/1981 United Kingdom .
2137988 10/1984 United Kingdom .

Primary Examiner—Paul J. Killos
Attorney, Agent, or Firm—Sprung Horn Kramer & Woods

[57] ABSTRACT

Herbicidally active phenoxybenzoic acid esters of the formula

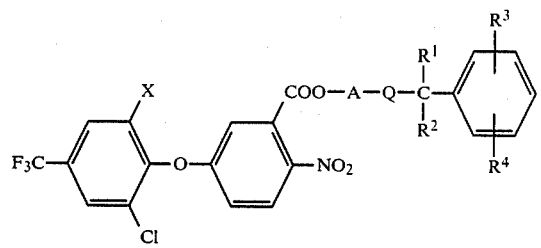

in which
X represents hydrogen or halogen,
A represents optionally branched $C_2$–$C_6$-alkanediyl,
Q represents oxygen, sulphur, sulphinyl (SO) or sulphonyl ($SO_2$),
$R^1$ represents hydrogen or methyl,
$R^2$ represents hydrogen or $C_1$–$C_4$-alkyl, and
$R^3$ and $R^4$ are identical or different and represent hydrogen, halogen, cyano, nitro, $C_1$–$C_4$-alkyl, halogeno-$C_1$–$C_2$-alkyl, $C_1$–$C_4$-alkoxy, halogeno-$C_1$–$C_2$-alkoxy and $C_1$–$C_2$-alkoxycarbonyl.

12 Claims, No Drawings

PHENOXYBENZOIC ACID ESTER HERBICIDES

The invention relates to new phenoxybenzoic acid esters, a process for the preparation of these, and the use of these as herbicides.

It has already been disclosed that numerous phenoxybenzoic acid derivatives have herbicidal properties (cf. U.S. Pat. No. 4,063,929). Thus, for example, the sodium salt of 3-(2-chloro-4-trifluoromethyl-phenoxy)-6-nitrobenzoic acid can be employed for combating weeds. The action of this substance is good, but some weeds are not always fully covered at low application rates.

New phenoxybenzoic acid esters of the formula (I)

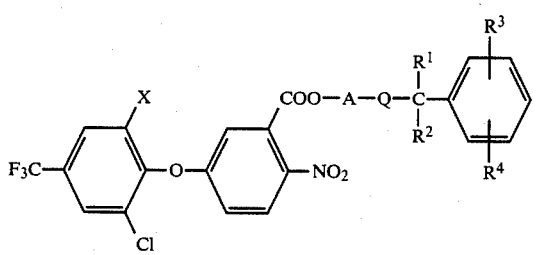

in which
X represents hydrogen or halogen,
A represents optionally branched $C_2-C_6$-alkanediyl,
Q represents oxygen, sulphur, sulphinyl (SO) or sulphonyl ($SO_2$),
$R^1$ represents hydrogen or methyl,
$R^2$ represents hydrogen or $C_1-C_4$-alkyl, and
$R^3$ and $R^4$ are identical or different and represent hydrogen, halogen, cyano, nitro, $C_1-C_4$-alkyl, halogeno-$C_1-C_2$-alkyl, $C_1-C_4$-alkoxy, halogeno-$C_1-C_2$-alkoxy and $C_1-C_2$-alkoxycarbonyl,
have now been found.

In the case where A represents branched $C_2-C_6$-alkanediyl, the phenoxybenzoic acid esters of the formula (I) contain at least one asymmetrically substituted carbon atom and can therefore exist in various enantiomeric forms. The invention relates both to the possible individual isomers and to mixtures of these isomers.

It has furthermore been found that phenoxybenzoic acid esters of the formula (I) are obtained when (a) phenoxybenzoyl chlorides of the formula (II)

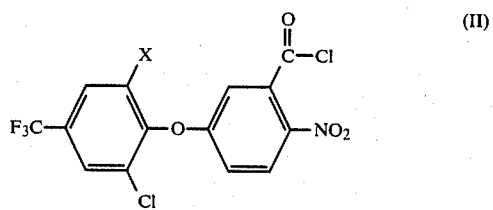

in which X has the abovementioned meaning, are reacted with hydroxyl compounds of the formula (III)

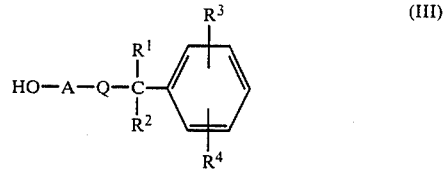

in which A, Q, $R^1$, $R^2$, $R^3$ and $R^4$ have the abovementioned meanings, if appropriate in the presence of an acid-binding agent and if appropriate in the presence of a diluent, or, in addition, if compounds of the formula (I) in which Q represents sulphinyl or sulphonyl are to be prepared, when
(b) the compounds of the formula (Ia)

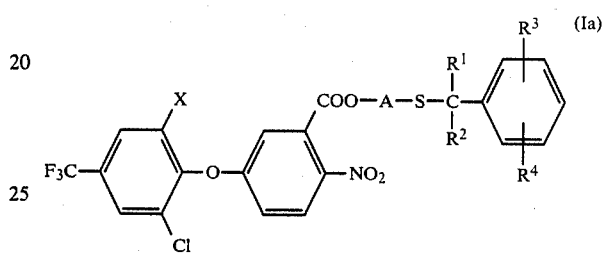

in which A, X, $R^1$, $R^2$, $R^3$ and $R^4$ have the abovementioned meanings, are reacted with oxidants, if appropriate in the presence of a catalyst and if appropriate in the presence of a diluent.

Finally, it has been found that the new phenoxybenzoic acid esters of the formula (I) are distinguished by an excellent herbicidal action.

Surprisingly, the phenoxybenzoic acid esters of the formula (I) according to the invention are considerably more effective against some important weeds and have significantly better selective properties than the sodium salt of 3-(2-chloro-4-trifluoromethyl-phenoxy)-6-nitrobenzoic acid, which is a structurally similar, previously known active compound of analogous direction of action.

Formula (I) provides a general definition of the phenoxybenzoic acid esters according to the invention. Preferred compounds of the formula (I) are those in which
X represents hydrogen, fluorine or chlorine,
A represents optionally branched $C_2-C_5$-alkanediyl,
Q represents oxygen, sulphur, sulphinyl or sulphonyl,
$R^1$ represents hydrogen,
$R^2$ represents hydrogen or methyl, and
$R^3$ and $R^4$ are identical or different and represent hydrogen, fluorine, chlorine, cyano, nitro, methyl, trifluoromethyl, methoxy, trifluoromethoxy or methoxycarbonyl.

Particularly preferred compounds of the formula (I) are those in which
X represents hydrogen or chlorine,
A represents optionally branched $C_2-C_5$-alkanediyl,
Q represents oxygen, sulphur or sulphonyl,
$R^1$ represents hydrogen,
$R^2$ represents hydrogen or methyl, and
$R^3$ and $R^4$ are identical or different and represent hydrogen, fluorine, chlorine or methoxy.

If 3-(2,6-dichloro-4-trifluoromethyl-phenoxy)-6-nitro-benzoyl chloride and 2-benzyloxy-ethanol are used as starting materials for process (a) according to the invention, the course of process (a) according to the invention may be represented by the following equation:

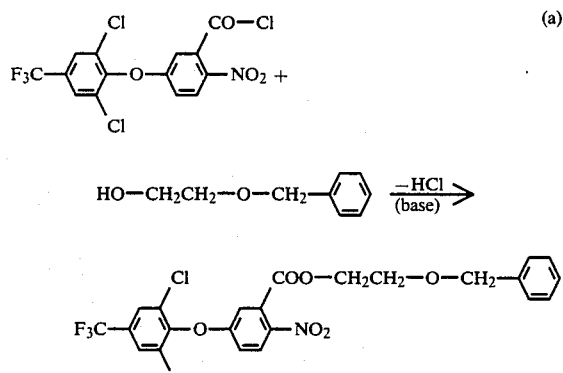

If 2-benzylthio-ethyl 5-(2,6-dichloro-4-trifluoromethyl-phenoxy)-2-nitro-benzoate is used as starting material and hydrogen peroxide is used as oxidant for process (b) according to the invention, the course of process (b) according to the invention may be represented by the following equation:

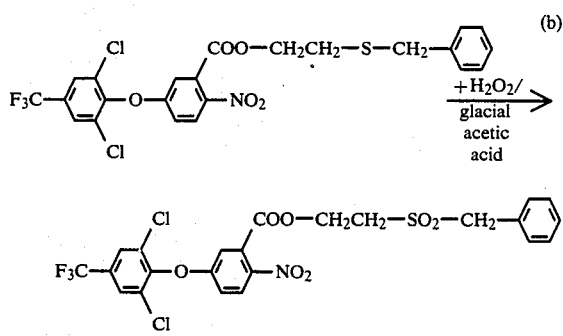

Formula (II) provides a definition of the phenoxybenzoyl chlorides required as starting materials in process (a) according to the invention. In this formula, X preferably has those meanings which have already been mentioned in connection with the description of the compounds of the formula (I) according to the invention as being preferred for this radical.

The following may be mentioned as examples of compounds of the formula (II): 3-(2-chloro-4-trifluoromethyl-phenoxy)-6-nitro-benzoyl chloride, 3-(2,6-dichloro-4-trifluoromethyl-phenoxy)-6-nitro-benzoyl chloride and 3-(2-chloro-6-fluoro-4-trifluoromethyl-phenoxy)-6-nitro-benzoyl chloride.

The phenoxybenzoyl chlorides of the formula (II) are known or can be prepared in a simple fashion by known processes (cf. DE-OS (German Published Specification) No. 2,311,638, EP-OS (European Published Specification) No. 63,741 and EP-OS (European Published Specification) No. 122,037).

Formula (III) provides a definition of the hydroxyl compounds furthermore required as starting materials in process (a) according to the invention. In this formula, A, Q, $R^1$, $R^2$, $R^3$ and $R^4$ preferably have those meanings which have already been mentioned in connection with the description of substances of the formula (I) according to the invention as being preferred for these radicals.

The following may be mentioned as examples of compounds of the formula (III):

TABLE 1

$$\text{HO—A—Q—}\underset{R^2}{\overset{R^1}{\text{C}}}\text{—} \text{(phenyl with } R^3, R^4\text{)} \quad (III)$$

| A | Q | $R^1$ | $R^2$ | $R^3$ | $R^4$ |
|---|---|---|---|---|---|
| —CH$_2$CH$_2$— | O | H | H | H | H |
| —CH$_2$CH$_2$— | S | H | H | H | H |
| —CH$_2$CH$_2$— | SO$_2$ | H | H | H | H |
| —(CH$_2$)$_3$— | O | H | H | H | H |
| —(CH$_2$)$_3$— | S | H | H | H | H |
| —(CH$_2$)$_3$— | SO$_2$ | H | H | H | H |
| —CH(CH$_3$)—CH$_2$— | O | H | H | H | H |
| —CH(CH$_3$)—CH$_2$— | S | H | H | H | H |
| —CH(CH$_3$)—CH$_2$— | SO$_2$ | H | H | H | H |
| —CH$_2$—C(CH$_3$)$_2$—CH$_2$— | O | H | H | H | H |
| —CH$_2$—C(CH$_3$)$_2$—CH$_2$— | S | H | H | H | H |
| —CH$_2$—C(CH$_3$)$_2$—CH$_2$— | SO$_2$ | H | H | H | H |
| —CH$_2$CH$_2$— | O | H | H | 2-Cl | H |
| —CH$_2$CH$_2$— | O | CH$_3$ | H | H | H |
| —CH$_2$CH$_2$— | S | CH$_3$ | H | H | H |
| —CH$_2$CH$_2$— | O | H | H | 2-Cl | 6-Cl |
| —CH$_2$CH$_2$— | O | H | H | 4-F | H |
| —CH$_2$CH$_2$— | S | H | H | 4-F | H |
| —CH$_2$CH$_2$— | O | H | H | 4-Cl | H |
| —CH$_2$CH$_2$— | S | H | H | 4-Cl | H |
| —CH$_2$CH$_2$— | SO$_2$ | H | H | 4-Cl | H |
| —CH$_2$CH$_2$— | O | H | H | 4-OCH$_3$ | H |
| —CH$_2$CH$_2$— | S | H | H | 4-OCH$_3$ | H |
| —CH$_2$CH$_2$— | O | H | H | 2-F | H |
| —CH$_2$CH$_2$— | S | H | H | 2-F | H |
| —CH$_2$CH$_2$— | O | H | H | 2-F | 6-F |
| —CH$_2$CH$_2$— | S | H | H | 2-F | 6-F |
| —CH$_2$CH$_2$— | O | H | H | 4-CH$_3$ | H |

The compounds of the formula (III) are known or can be prepared in a simple fashion by known processes (cf. EP-OS (European Published Specification) No. 68,260 and EP-OS (European Published Specification) No. 92,112).

Process (a), according to the invention, for the preparation of the new phenoxybenzoic acid esters of the formula (I) is preferably carried out using diluents. Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl, methyl isopropyl and methyl isobutyl ketone, esters, such as methyl and ethyl acetates, nitriles, such as, for example, acetonitrile and propionitrile amides, such as, for example, dimethylformamide, dimethylacetamide and N-methyl-pyrrolidone, and also dimethyl suphoxide and tetramethylene sulphone.

All acid-binding agents which can usually be used for such reactions can be employed as acid-binding agents in process (a) according to the invention. Alkali metal hydroxides, such as, for example, sodium hydroxide and potassium hydroxide, alkaline-earth metal hydroxides, such as, for example, calcium hydroxide, alkali metal carbonates and alcoholates, such as sodium carbonate and potassium carbonate, sodium methylate and ethylate and potassium methylate and ethylate, furthermore aliphatic, aromatic or heterocyclic amines, for example triethylamine, trimethylamine, dimethylaniline, dimethylbenzylamine, pyridine, 1,5-diaza-bicyclo-[4,3,0]-non-5-ene (DBN) and 1,8-diazabicyclo-[5,4,0]-undec-7-ene (DBU), are preferably suitable.

The reaction temperatures may be varied within a relatively wide range in process (a), according to the invention, for the preparation of the phenoxybenzoic acid esters of the formula (I). In general, the process is carried out at temperatures between −20° C. and +100° C., preferably at temperatures between 0° C. and 80° C.

Process (a) according to the invention is generally carried out under atmospheric pressure. However, it is also possible to carry out the process under increased or reduced pressure.

The starting materials required in each case are generally employed in approximately equimolar amounts in order to carry out process (a) according to the invention. However, it is also possible to use one of the two components employed in each case in a relatively large excess. The reactions are generally carried out in a suitable diluent in the presence of an acid acceptor, and the reaction mixture is stirred for several hours at the temperature required in each case. In process (a) according to the invention, work-up is carried out in each case by conventional methods.

Formula (Ia) provides a general definition of the compounds to be used as starting materials in process (b) according to the invention. In this formula (Ia), X, A, $R^1$, $R^2$, $R^3$ and $R^4$ preferably represent those radicals which have already been mentioned in connection with the description of the substances of the formula (I) according to the invention as being preferred for these substituents.

The following may be mentioned as examples of compounds of formula (Ia):

TABLE 2

(Ia) structure: $F_3C$-substituted phenyl with X and Cl, linked via O to phenyl with $NO_2$ and COO—A—S—C($R^1$)($R^2$)-phenyl with $R^3$, $R^4$

| X  | A | $R^1$ | $R^2$ | $R^3$ | $R^4$ |
|----|---|-------|-------|-------|-------|
| H  | —CH$_2$CH$_2$— | H | H | H | H |
| Cl | —CH$_2$CH$_2$— | H | H | H | H |
| H  | —(CH$_2$)$_3$— | H | H | H | H |
| Cl | —(CH$_2$)$_3$— | H | H | H | H |
| H  | —CH(CH$_3$)—CH$_2$— | H | H | H | H |
| Cl | —CH(CH$_3$)—CH$_2$— | H | H | H | H |
| H  | —CH$_2$—C(CH$_3$)$_2$—CH$_2$— | H | H | H | H |
| Cl | —CH$_2$—C(CH$_3$)$_2$—CH$_2$— | H | H | H | H |
| H  | —CH$_2$CH$_2$— | CH$_3$ | H | H | H |
| Cl | —CH$_2$CH$_2$— | CH$_3$ | H | H | H |
| H  | —CH$_2$CH$_2$— | H | H | 4-F | H |
| Cl | —CH$_2$CH$_2$— | H | H | 4-F | H |
| H  | —CH$_2$CH$_2$— | H | H | 4-Cl | H |
| Cl | —CH$_2$CH$_2$— | H | H | 4-Cl | H |
| H  | —CH$_2$CH$_2$— | H | H | 4-OCH$_3$ | H |
| Cl | —CH$_2$CH$_2$— | H | H | 4-OCH$_3$ | H |
| H  | —CH$_2$CH$_2$— | H | H | 2-F | H |
| Cl | —CH$_2$CH$_2$— | H | H | 2-F | H |
| H  | —CH$_2$CH$_2$— | H | H | 2-F | 6-F |
| Cl | —CH$_2$CH$_2$— | H | H | 2-F | 6-F |
| H  | —CH$_2$CH$_2$— | H | H | 4-CH$_3$ | H |
| Cl | —CH$_2$CH$_2$— | H | H | 4-CH$_3$ | H |

The compounds of the formula (Ia) are compounds according to the invention and are prepared according to process (a).

All conventional oxygen-donating oxidants can be employed as oxidants for process (b) according to the invention. Hydrogen peroxide, peracetic acid, m-chloroperbenzoic acid and "chlorine bleach" or "chlorine water" (Cl$_2$/H$_2$O) are preferably suitable.

Suitable diluents for carrying out process (b) according to the invention are all organic solvents which can usually be used for such oxidations. Water, glacial acetic acid, choloroform or methylene chloride can preferably be used.

All reaction accelerators which can usually be used for such oxidations can be employed as catalysts in process (b) according to the invention. Formic acid, sulphuric acid and ammonium molybdate can preferably be used. The process is preferably carried out without catalyst.

The reaction temperatures may be varied within a relatively wide range in process (b) according to the invention. In general, the process is carried out at temperatures between −20° C. and +80° C., preferably at temperatures between 0° C. and 50° C. Process (b) according to the invention is generally carried out under atmospheric pressure.

Between 1 and 5 moles of oxidant are employed per mole of the compound of the formula (Ia) when carrying out process (b) according to the invention. The reaction is generally carried out in a diluent and if appropriate in the presence of catalysts. Work-up is effected by conventional methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The new active compounds of the formula (I) are suitable for selective combating of dicotyledon weeds in mono- and dicotyledon cultures such as, for example, wheat and soybeans, in particular in the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Known herbicides, such as, for example, N-(2-benzothiazolyl)-N,N'-dimethylurea, 3-(4-isopropylphenyl)-1,1-dimethylurea, 2-chloro-N-{[(4-methoxy-6-methyl-1,3,5-triazin-2-yl)-amino]-carbonyl}-benzenesulphonamide, ethyl 2-{[(4-chloro-6-methoxy-2-pyrimidyl)-aminocarbonyl]aminosulphonyl}-benzoate, 2- ethylamino-6-(1,1-dimethylethyl-amino)-4-methylthio-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, methyl 2-[4-(2,4-dichlorophenoxy)-phenoxy]-propionate, 2-{4-[(3-chloro-5-trifluoromethyl-2-pyridinyl)oxy]-phenoxy}-propionic acid, the R enantiomer of (trimethylsilyl)-methyl 2-{4-[(3,5-dichloro-2-pyridinyl)oxy]-phenoxy}-propionate, 2,4-dichlorophenoxyacetic acid, 2-(2,4-dichlorophenoxy)-propionic acid, 4-chloro-2-methylphenoxy-acetic acid, 2-(4-chloro-2-methyl-phenoxy)-propionic acid, 3,5-diiodo-4-hydroxy-benzonitrile, 3,5-dibromo-4-hydroxy-benzonitrile, 2-[5-methyl-5-(1-methylethyl)-4-oxo-2-imidazolin-2-yl]-3-pyridinecarboxylic acid, 2-(1-ethoxyamino-butylidene)-5-(2-ethylthiopropyl)-cyclohexane-1,3-dione, 2-[1-(ethoxyimino)-butyl]-3-hydroxy-5-(tetrahydro-2H-thiopyran-3-yl)-2-cyclohexen-1-one, the sodium salts of 2-(1-alloxyaminobutylidene)-4-methoxycarbonyl-5,5-dimethylcyclohexane-1,3-dione, [(4-amino-3,5-dichloro-6-fluoro-2-pyridyl)oxy]-acetic acid and 3-isopropyl-2,1,3-benzothiadiazin-4-one 2,2-dioxide, can be used for the mixtures. Surprisingly, some mixtures also have a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They are preferably applied after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

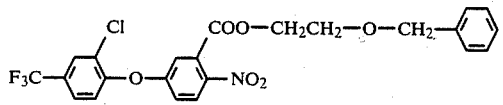

(Process (a))

A solution of 7.6 g (0.02 mol) of 5-(2-chloro-4-trifluoromethyl-phenoxy)-2-nitro-benzoyl chloride in 50 ml of methylene chloride is added dropwise with stirring to a mixture of 3.0 g (0.02 mol) of 2-benzyloxy-ethanol, 2 g of pyridine and 50 ml of methylene chloride, the internal temperature being kept at 0° C. to +5° C. The reaction mixture is then stirred for 20 hours at 20° C., washed with 1N hydrochloric acid and soda solution, dried using sodium sulphate and filtered. The solvent is carefully removed from the filtrate by distillation in a water-pump vacuum, and the residue is brought to crystallization by trituration with n-hexane, and the product is isolated by filtering off under suction.

5.7 g (58% of theory) of 2-benzyloxy-ethyl 5-(2-chloro-4-trifluoromethyl-phenoxy)-2-nitro-benzoate are obtained in the form of white crystals of melting point 85° C.

The compound of Example (1) can also be prepared by process (a) as follows:

A solution of 121 g (1.20 mols) of triethylamine in 100 ml of toluene is added over about 2 hours to a mixture of 380 g (1.00 mol) of 5-(2-chloro-4-trifluoromethyl-phenoxy)-2-nitro-benzoyl chloride, 160 g (1.05 mol) of 2-benzyloxy-ethanol and 2 liters of toluene at 20° C. to 40° C. with stirring. The reaction mixture is then stirred for about a further 4 hours at 30° C. to 40° C., subsequently washed twice with cold 1N hydrochloric acid and twice with cold saturated soda solution, dried using sodium sulphate and filtered. The solvent is carefully removed from the filtrate by distillation in a water-pump vacuum, the residue is brought to crystallization by trituration with n-hexane, and the product is isolated by filtering off under suction.

436 g (88% of theory) of 2-benzyloxy-ethyl 5-(2-chloro-4-trifluoromethyl-phenoxy)-2-nitro-benzoate are obtained in the form of white crystals of melting point 85° C.

EXAMPLE 2

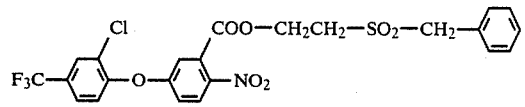

(Process (b))

10 g of a 35% strength aqueous solution of hydrogen peroxide (0.10 mol of $H_2O_2$) are added dropwise with stirring to a mixture of 10.2 g (0.02 mol) of 2-benzylthio-ethyl 5-(2-chloro-4-trifluoromethyl-phenoxy)-2-nitro-benzoate and 100 ml of glacial acetic acid at 20° C. to 40° C. The reaction mixture is stirred at 40° C. for 3 hours, diluted with methylene chloride to about twice the volume, washed with aqueous sodium hydrogen sulphite solution, then washed in water, dried with sodium sulphate and filtered. The solvent is carefully removed from the filtrate by distillation in a water-pump vacuum.

6.8 g (63% of theory) of 2-benzylsulphonylethyl 5-(2-chloro-4-trifluoromethyl-phenoxy)-2-nitro-benzoate of melting point 105° C. are obtained.

The compounds of the formula (I) listed in Table 3 below can be prepared analogously to Example 1 and 2 or analogously to processes (a) and (b):

TABLE 3

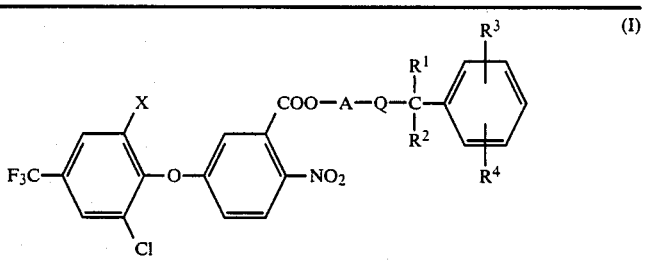

| Example No. | X | A | Q | R¹ | R² | R³ | R⁴ | Physical constants |
|---|---|---|---|---|---|---|---|---|
| 3 | Cl | —CH₂CH₂— | S | H | H | H | H | $n_D^{20}$: 1.5782 |
| 4 | Cl | —(CH₂)₃— | O | H | H | H | H | amorphous |
| 5 | H | —(CH₂)₃— | O | H | H | H | H | $n_D^{20}$: 1.5546 |
| 6 | Cl | —CH₂CH₂— | O | H | H | H | H | $n_D^{20}$: 1.5580 |
| 7 | H | —CH₂CH₂— | S | H | H | H | H | $n_D^{20}$: 1.5785 |
| 8 | H | —CH₂CH₂— | O | H | H | 2-Cl | H | m.p. 87° C. |
| 9 | H | —CH₂—C(CH₃)(CH₃)—CH₂— | O | H | H | H | H | $n_D^{20}$: 1.5408 |
| 10 | Cl | —CH₂CH₂— | O | H | H | 4-F | H | |
| 11 | H | —CH₂CH₂— | O | H | H | 4-F | H | |
| 12 | Cl | —CH₂CH₂— | O | H | H | 2-Cl | 6-Cl | |
| 13 | H | —CH₂CH₂— | O | H | H | 2-Cl | 6-Cl | |
| 14 | Cl | —CH(CH₃)—CH₂— | O | H | H | H | H | |
| 15 | H | —CH(CH₃)—CH₂— | O | H | H | H | H | |
| 16 | Cl | —CH₂CH₂— | O | H | H | 2-F | H | |
| 17 | H | —CH₂CH₂— | O | H | H | 2-F | H | |
| 18 | Cl | —CH₂CH₂— | O | H | CH₃ | H | H | |
| 19 | H | —CH₂CH₂— | O | H | CH₃ | H | H | |
| 20 | Cl | —CH₂CH₂— | S | H | H | 4-Cl | H | |
| 21 | H | —CH₂CH₂— | S | H | H | 4-OCH₃ | H | |
| 22 | Cl | —CH₂CH₂— | SO₂ | H | H | H | H | |

Use Example

In the following use example, the compound shown below is used as the comparison substance:

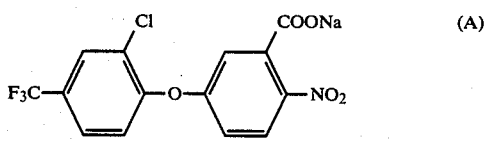

Sodium salt of 3-(2-chloro-4-trifluoromethyl-phenoxy)-6-nitro-benzoic acid (known from U.S. Pat. No. 4,063,929).

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the active compound according to Example (1), for example, exhibits a better activity than comparison substance (A) for combating dicotyledon weeds, such as, for example, Chenopodium, Sida and Viola, in wheat and soybeans.

It will be understood that the specification and examples are illustrative but not limitative of the present invention and that other embodiments within the spirit and scope of the invention will suggest themselves to those skilled in the art.

We claim:

1. A phenoxybenzoic acid ester of the formula

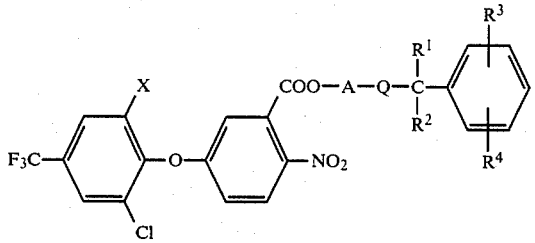

in which
X represents hydrogen or halogen,
A represents optionally branched $C_2$-$C_6$-alkanediyl,
Q represents oxygen, sulphur, sulphinyl (SO) or sulphonyl (SO$_2$),
$R^1$ represents hydrogen or methyl,
$R^2$ represents hydrogen or $C_1$-$C_4$-alkyl, and
$R^3$ and $R^4$ are identical or different and represent hydrogen, halogen, cyano, nitro, $C_1$-$C_4$-alkyl, halogeno-$C_1$-$C_2$-alkyl, $C_1$-$C_4$-alkoxy, halogeno-$C_1$-$C_2$-alkoxy and $C_1$-$C_2$-alkoxycarbonyl.

2. A phenoxybenzoic acid ester according to claim 1, in which
X represents hydrogen, fluorine or chlorine,
A represents optionally branched $C_2$-$C_5$-alkanediyl,
Q represents oxygen, sulphur, sulphinyl or sulphonyl,
$R^1$ represents hydrogen,
$R^2$ represents hydrogen or methyl, and
$R^3$ and $R^4$ are identical or different and represent hydrogen, fluorine, chlorine, cyano, nitro, methyl, trifluoromethyl, methoxy, trifluoromethoxy or methoxycarbonyl.

3. A phenoxybenzoic acid ester according to claim 1, in which
X represents hydrogen or chlorine,
A represents optionally branched $C_2$-$C_5$-alkanediyl,
Q represents oxygen, sulphur or sulphonyl,
$R^1$ represents hydrogen,
$R^2$ represent hydrogen or methyl, and
$R^3$ and $R^4$ are identical or different and represent hydrogen, fluorine, chlorine or methoxy.

4. An ester according to claim 1, wherein such ester is 2-benzyloxy-ethyl 5-(2-chloro-4-trifluoromethyl-phenoxy)-2-nitro-benzoate of the formula

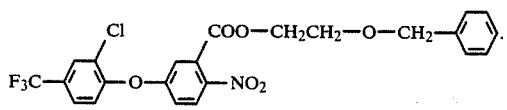

5. An ester according to claim 1, wherein such ester is 2-benzylthioethyl 5-(2,6-dichloro-4-trifluoromethyl-phenoxy)-2-nitro-benzoate of the formula

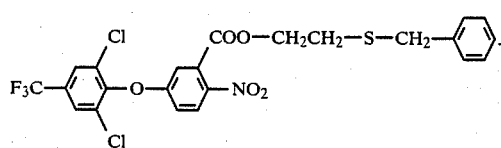

6. An ester according to claim 1, wherein such ester is 3-benzyloxypropyl 5-(2,6-dichloro-4-trifluoromethyl-phenoxy)-2-nitro-benzoate of the formula

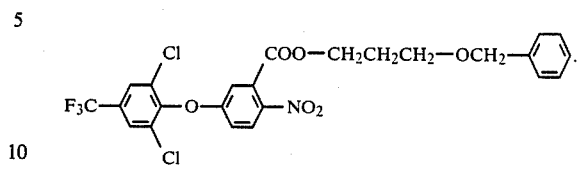

7. An ester according to claim 1, wherein such ester is 3-benzyloxypropyl 5-(2-chloro-4-trifluoromethyl-phenoxy)-2-nitro-benzoate of the formula

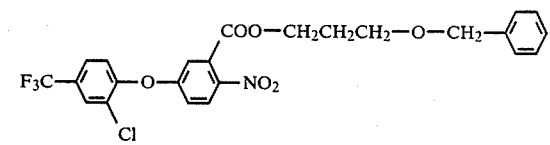

8. An ester according to claim 1, wherein such ester is 2-benzyloxyethyl 5-(2,6-dichloro-4-trifluoromethyl-phenoxy)-2-nitro-benzoate of the formula

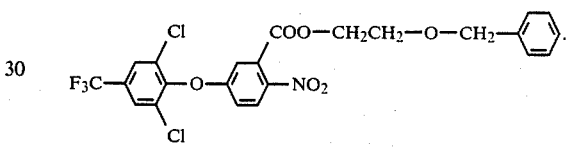

9. An ester according to claim 1, wherein such ester is 2-benzylthioethyl 5-(2-chloro-4-trifluoromethyl-phenoxy)-2-nitro-benzoate of the formula

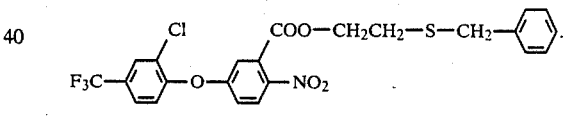

10. A herbicidal composition comprising a herbicidally effective amount of an ester according to claim 1 and a diluent.

11. A method of combating unwanted vegetation which comprises applying to such vegetation or to a locus from which it is desired to exclude such vegetation a herbicidally effective amount of a compound according to claim 1.

12. The method according to claim 11 wherein such compound is
2-benzyloxy-ethyl 5-(2-chloro-4-trifluoromethyl-phenoxy)-2-nitro-benzoate,
2-benzylthioethyl 5-(2,6-dichloro-4-trifluoromethyl-phenoxy)-2-nitro-benzoate,
3-benzyloxypropyl 5-(2,6-dichloro-4-trifluoromethyl-phenoxy)-2-nitro-benzoate,
3-benzyloxypropyl 5-(2-chloro-4-trifluoromethyl-phenoxy)-2-nitro-benzoate,
2-benzyloxyethyl 5-(2,6-dichloro-4-trifluoromethyl-phenoxy)-2-nitro-benzoate or
2-benzylthioethyl 5-(2-chloro-4-trifluoromethyl-phenoxy)-2-nitro-benzoate.

* * * * *